United States Patent
Ji et al.

(10) Patent No.: US 8,095,724 B2
(45) Date of Patent: Jan. 10, 2012

(54) METHOD OF WEAR LEVELING FOR NON-VOLATILE MEMORY AND APPARATUS USING VIA SHIFTING WINDOWS

(75) Inventors: Yung Li Ji, Hsinchu (TW); Chia Chen Chang, Hsinchu (TW); Chih Nan Yen, Hsinchu (TW); Fuja Shone, Hsinchu (TW)

(73) Assignee: Skymedi Corporation, Hsinchu (TW)

( * ) Notice: Subject to any disclaimer, the term of this patent is extended or adjusted under 35 U.S.C. 154(b) by 562 days.

(21) Appl. No.: 12/026,400

(22) Filed: Feb. 5, 2008

(65) Prior Publication Data
US 2009/0198882 A1    Aug. 6, 2009

(51) Int. Cl.
G06F 12/00    (2006.01)
G06F 13/00    (2006.01)
G06F 13/28    (2006.01)

(52) U.S. Cl. .......................................................... 711/103

(58) Field of Classification Search .................... 711/103
See application file for complete search history.

(56) References Cited

U.S. PATENT DOCUMENTS
2004/0044869 A1* 3/2004 Louie et al. .................... 711/165
2007/0294490 A1* 12/2007 Freitas et al. .................. 711/154
* cited by examiner Primary Examiner — Kevin Ellis
Assistant Examiner — Chad Davidson
(74) Attorney, Agent, or Firm — WPAT, P.C.; Anthony King

(57) ABSTRACT

A method of wear leveling for a non-volatile memory is disclosed. A non-volatile memory is divided into windows and gaps, with each gap between two adjacent windows. The windows comprise physical blocks mapped to logical addresses, and the gaps comprise physical blocks not mapped to logical addresses. The windows are shifted through the non-volatile memory in which the mapping to the physical blocks in the window to be shifted is changed to the physical blocks in the gap.

16 Claims, 7 Drawing Sheets

METHOD OF WEAR LEVELING FOR NON-VOLATILE MEMORY AND APPARATUS USING VIA SHIFTING WINDOWS

BACKGROUND OF THE INVENTION (A) Field of the Invention

The present invention is related to a method of wear leveling for a non-volatile memory and a wear leveling apparatus using the same.

(B) Description of Related Art

A non-volatile memory device such as ATA solid state disk or SD flash memory card may have an internal mapping from the received logical addresses to physical addresses of a non-volatile memory. In order to wear each physical block of non-volatile memory equally, the mapping changes during the running time because the host may need more time to write some specific LBA (Logical Block Addressing) addresses than other addresses. As shown in FIG. 1, a logical address (LBA) from the host 11 is converted into a physical address or PBA (Physical Block Addressing) by an address converter 12. The physical address is used for data read/write for a non-volatile memory 13 such as a flash memory. The address converter 12 may include a RAM 14 storing the mapping of logical addresses and physical addresses for inquiry by the address converter 12.

The RAM storing the mapping is crucial to the cost. A larger RAM increases the cost. Moreover, the wear leveling algorithm may not obtain all mapping data at one time if the RAM size is not large enough. Therefore, if the storage capacity of the RAM is insufficient, a window may be established to resolve the problem.

As shown in FIG. 2, a non-volatile memory is divided by multiple block groups, and different groups correspond to different windows. For instance, the wear leveling algorithm processes Block Group 0 first, and RAM stores only window 0's mapping data, and then the wear leveling algorithm processes Block Group 1 and the RAM stores only window 1's mapping data. Consequently, the RAM size can be fixed, even if the amount of mapping increases with the larger non-volatile memory. However, this method can make only the number of program/erase in the same window consistent, while the program/erase quantities of different windows may still be unbalanced.

SUMMARY OF THE INVENTION

The present invention provides a shifting wear leveling window. Even though the storage capacity of non-volatile memory devices increases with technology advances and the amount of required mapping increases, a RAM of fixed size and capable of storing relatively small amounts of mapping is sufficient to equalize the program/erase times of the entire non-volatile memory when the wear leveling algorithm of the non-volatile memory is in use. Moreover, the endurance may be different, depending upon the request. The present invention uses software to adjust the endurance of a non-volatile memory device, e.g., an SD card, having the non-volatile memory under the same hardware configuration.

According to the present invention, a non-volatile memory apparatus comprises a host, a non-volatile memory and an address converter. The address converter is configured to convert logical addresses from the host into physical addresses directed to physical blocks of the non-volatile memory. The address converter comprises a memory that stores mapping information between the logical addresses and the physical blocks.

In the present invention, a method of wear leveling for a non-volatile memory may perform on a basis of the non-volatile memory apparatus. The non-volatile memory is divided into windows and gaps, with a gap between every two adjacent windows. The windows comprise physical blocks mapping to logical addresses, and the gaps comprise physical blocks not mapping to logical addresses. The windows are shifted through the non-volatile memory in which the mapping to the physical blocks in the window to be shifted is changed to part or all of the physical blocks in the gap.

In a first embodiment, the logical addresses pointing to the physical blocks in the window to be shifted are changed to point to the physical blocks in the gap when shifting.

In a second embodiment, the window further comprises free physical blocks not mapping to logical addresses. The physical blocks in the window to be shifted are changed to be the free physical blocks before the window shift. The pointers to the free physical blocks are changed to point to the physical blocks in the gap when shifting.

The shifting of the first or second embodiments can be mixed, e.g., for shifting two blocks, one is conducted according to the first embodiment and the other is conducted according to the second embodiment.

The gap size is changeable so as to provide a suitable endurance of the non-volatile memory device having the non-volatile memory. Moreover, the number of useable physical blocks may be calculated. If there are not enough usable physical blocks, the window shift continues.

DETAILED DESCRIPTION OF THE INVENTION

Figure 1:
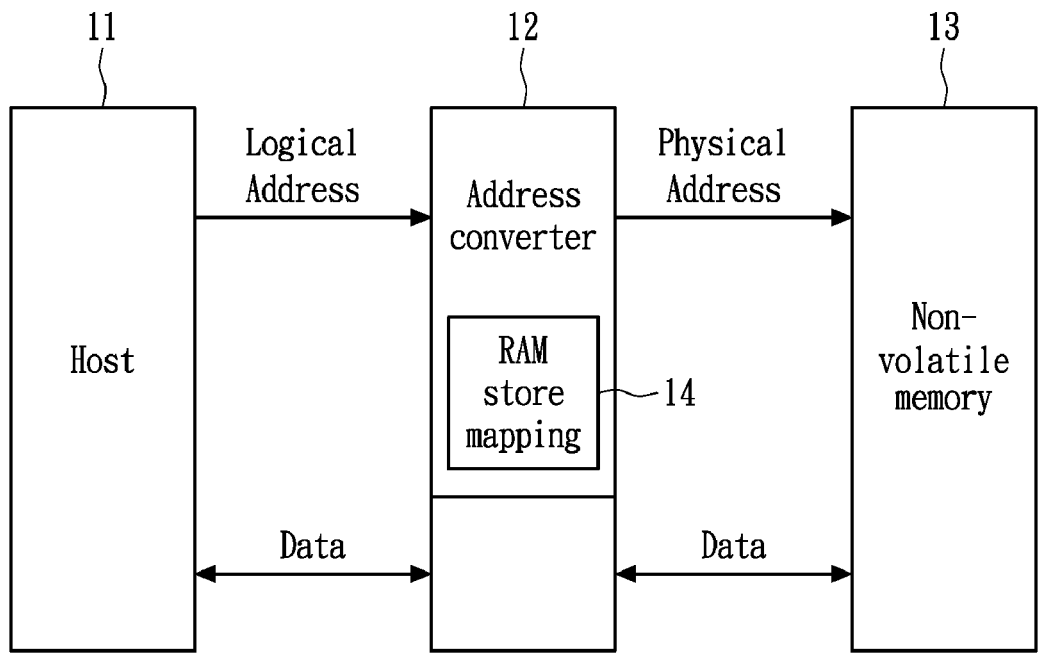
FIG. 1 shows a wear leveling apparatus for a non-volatile memory.
Figure 2:
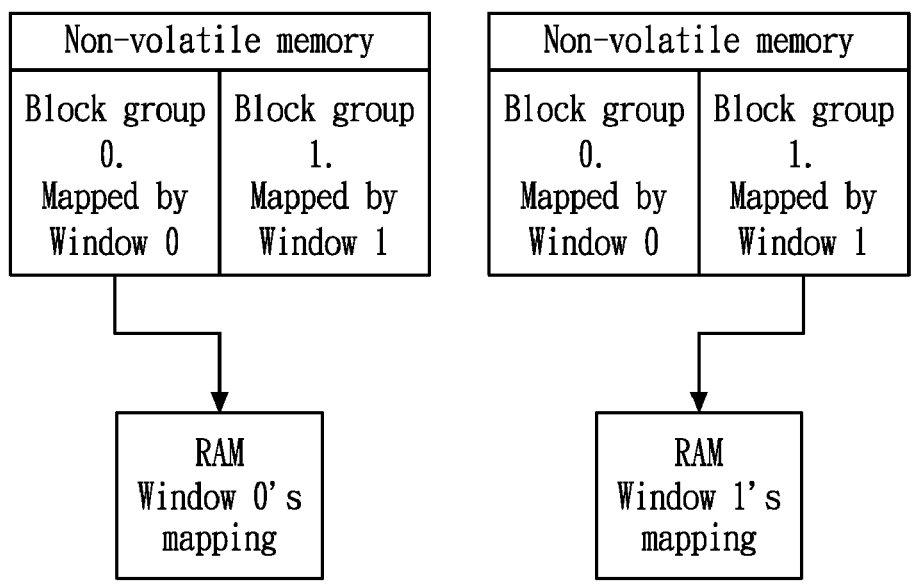
FIG. 2 shows separated windows in a non-volatile memory.

The present invention provides a novel wear leveling method that uses software to adjust the endurance of a non-volatile memory device under the same hardware configuration as that shown in FIG. 1.

Figure 3:
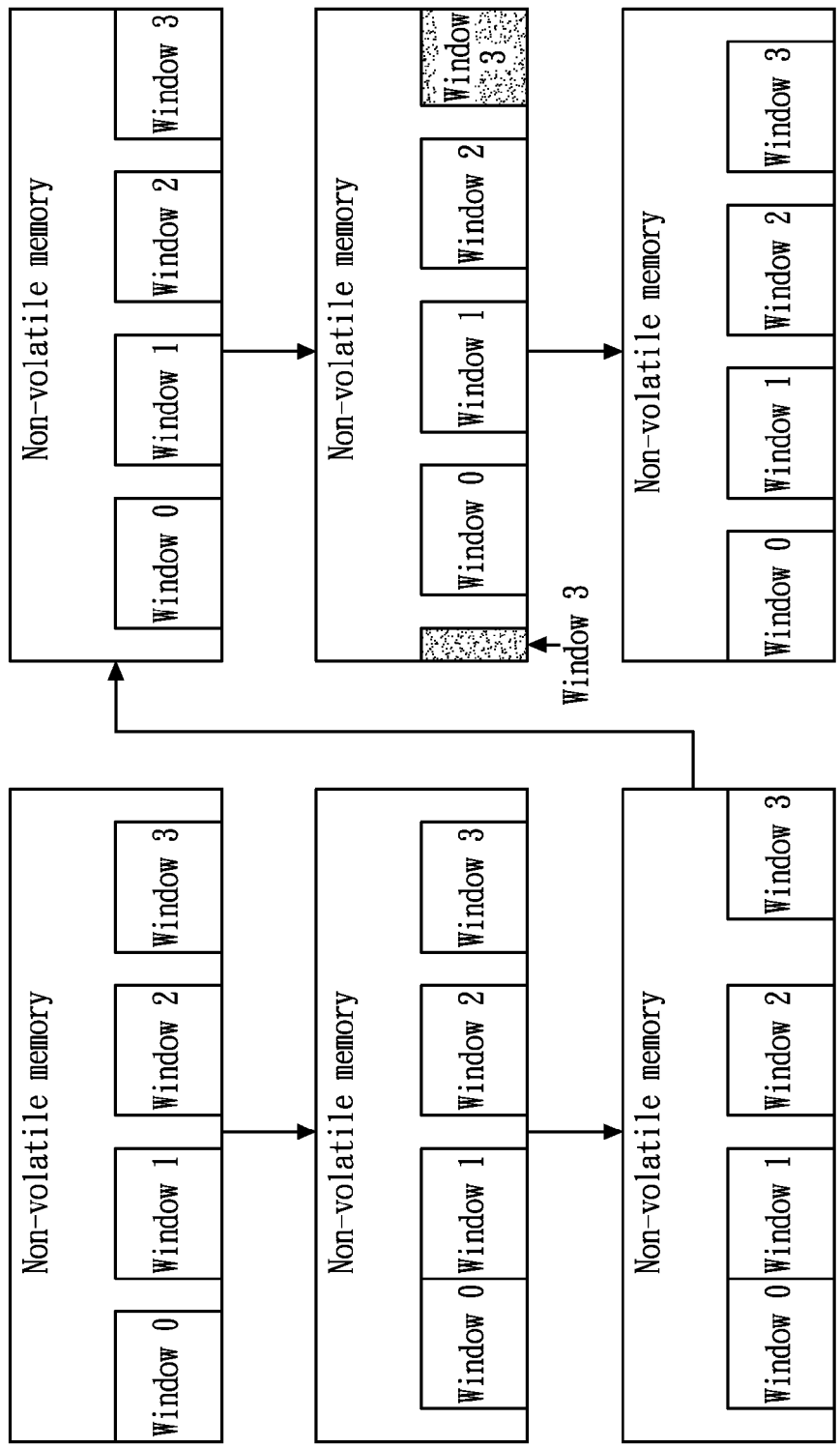
FIG. 3 shows the window shift of the method of wear leveling for a non-volatile memory in accordance with the present invention.

Referring to FIG. 3, initially, a non-volatile memory is divided into four windows, i.e., Windows 0, 1, 2 and 3. The windows do not occupy all non-volatile memory, and there are gaps between Windows 0 and 1, Windows 1 and 2, Windows 2 and 3, and Windows 3 and 0. Any wear leveling algorithm may be performed in each window. Next, Window 0 is shifted to be in contact with Window 1 at boundaries thereof, i.e., the gap between Window 0 and Window 1 is eliminated. Then, Window 3 is shifted right, and Window 2 and Window 1 are shifted at a suitable time. As a result, all the windows are shifted right with an offset of a gap. The shift can be repeated in which a portion of Window 3 is moved to the left of the non-volatile memory. After all the Windows are shifted, the windows rotate or run a cycle through the entire non-volatile memory and return to their original positions. If a window is programmed or erased more than a predetermined number of times, e.g., 2,400 times, the windows are shifted again. The windows are shifted through the entire non-volatile memory at least once before an erase/program endurance of the non-volatile memory device having the non-volatile memory is expired. In practice, the erase/program endurance may be predicted or predetermined. According to the present invention, a window shift does not move the complete window data, but rather a window is shifted by changing a small amount of mapping, which is described in detail below.

Figure 4:
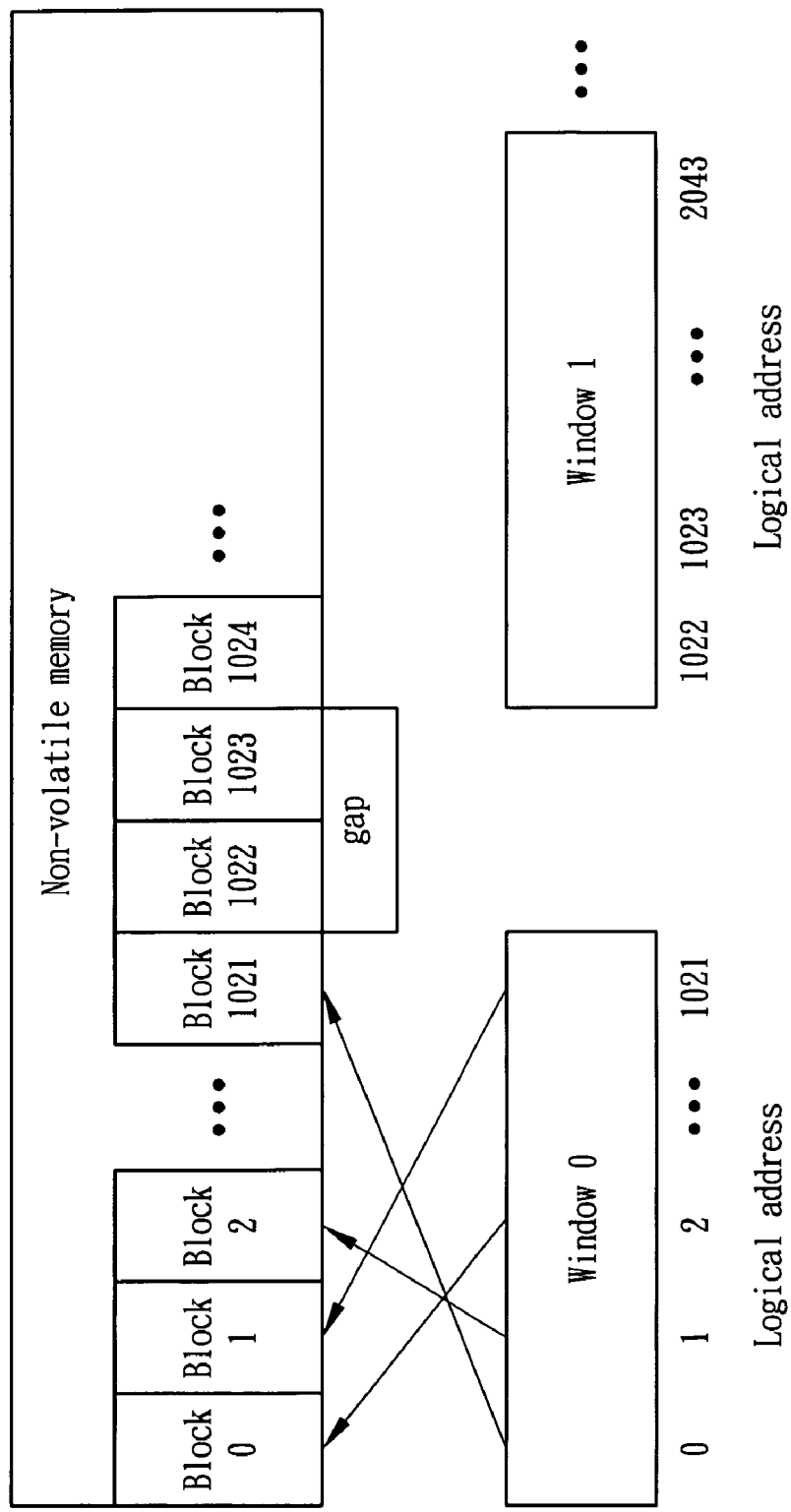
FIG. 4 and FIG. 5 show the method of wear leveling for a non-volatile memory in accordance with a first embodiment of the present invention.
Figure 5:
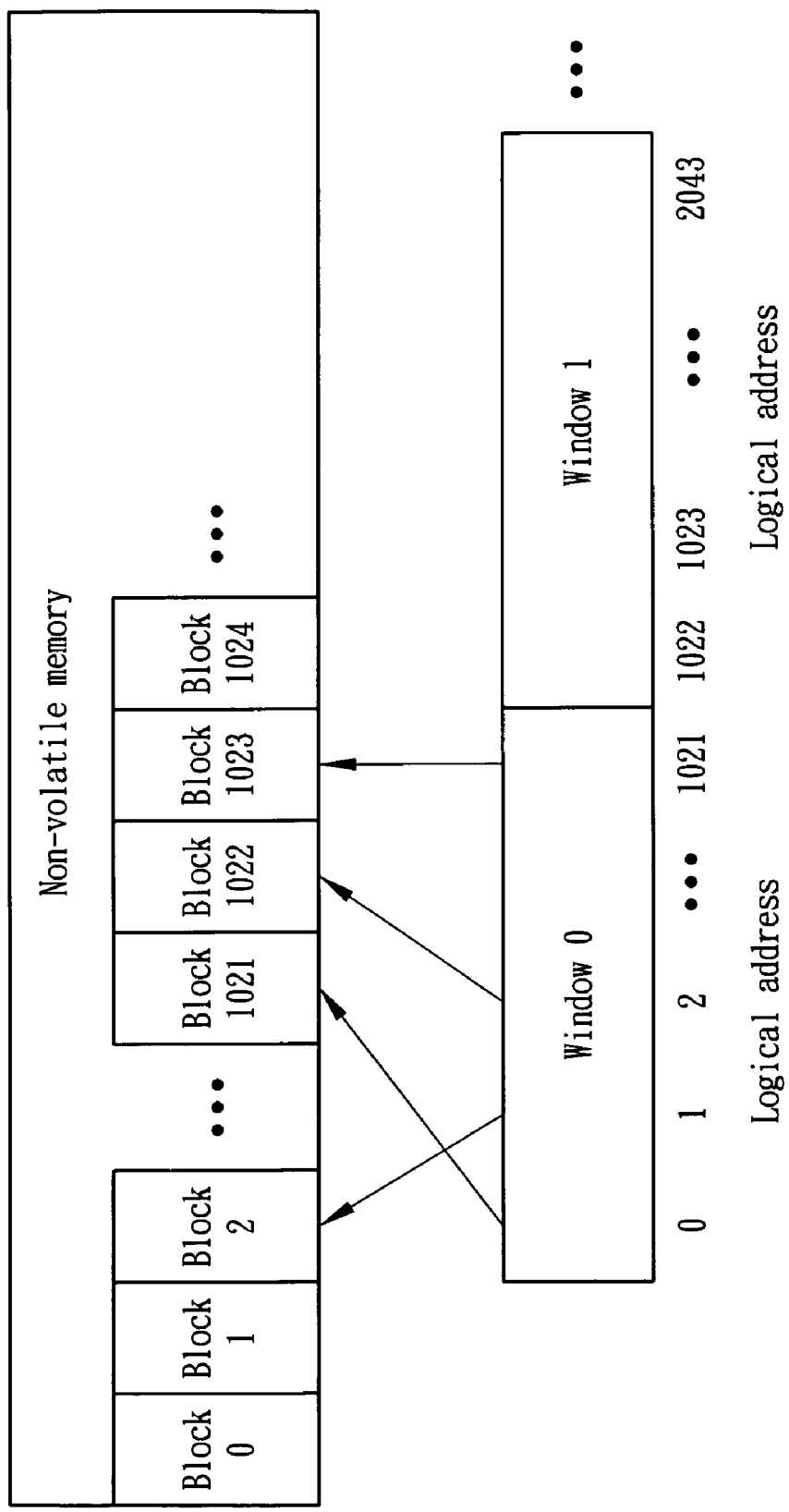

In accordance with current flash memory operation, a physical block may be pointed by logic addresses 0-255, and the next physical block may be pointed by logic addresses 256-511. Such mapping may be varied according to a new flash memory. Nevertheless, in consideration of clear illustration and description, one logic address pointing to one physical block is exemplified below. For a Multi Level Cell (MLC) flash, including 4,096 physical blocks (smallest erasable memory units) of an endurance of 5,000 program/erase cycles, each window includes 1,022 physical blocks and each gap comprises 2 physical blocks as shown in FIG. 4. The RAM for storing mapping information needs only to be of adequate size to store the mapping data for 1,022 physical blocks. Initially, Window 0 comprises physical block 0 to physical block 1021, and a gap between Window 0 and Window 1 comprises physical block 1022 and physical block 1023. The logical address 0 maps to physical block 1021, the logical address 1 maps to physical block 2, the logical address 2 maps to physical block 0, and the logical address 1021 maps to physical block 1. After Window 0 has been programmed and/or erased a predetermined number of times, e.g., Window 0 has been programmed and/or erased 2,400 times, Window 0 will shift 2 blocks as shown in FIG. 5. In accordance with the present invention, the shifting continues if an insufficient quantity of physical blocks can be erased and/or programmed in the window. After the shift, the logical addresses 2 and 1021 originally mapping to physical block 0 and physical block 1 are changed to map to physical block 1022 and physical block 1023 in the gap, while the other mappings are not changed. For example, the logical address 1 is originally mapped to physical block 2, and after the shift the logical address 1 still maps to physical block 2. In other words, data of the physical block 2 is not moved or changed. Consequently, the data movement is only two physical blocks, so that the impact to performance is negligible.

The program/erase times in a cycle can be calculated as follows.

1. 4,096 blocks/2 blocks=2,048 shifts
2. For each shift, a window undergoes at most 2,400 program/erase cycles.
3. Based on a good wear leveling algorithm, each block is programmed and/or erased 2,400/1,022=2.35 times.
4. Each block is programmed/erased at most 2.35×2,048=4,809 times during a whole window rotation.
5. Although the rotation increases the amount of data movement, the increase percentage is only around 2/2,400=0.08%.

Therefore, for the MLC flash having an endurance of 10,000 program/erase cycles to complete one or more rotations, the burden of the increase of data movement is very small.

Figure 6:
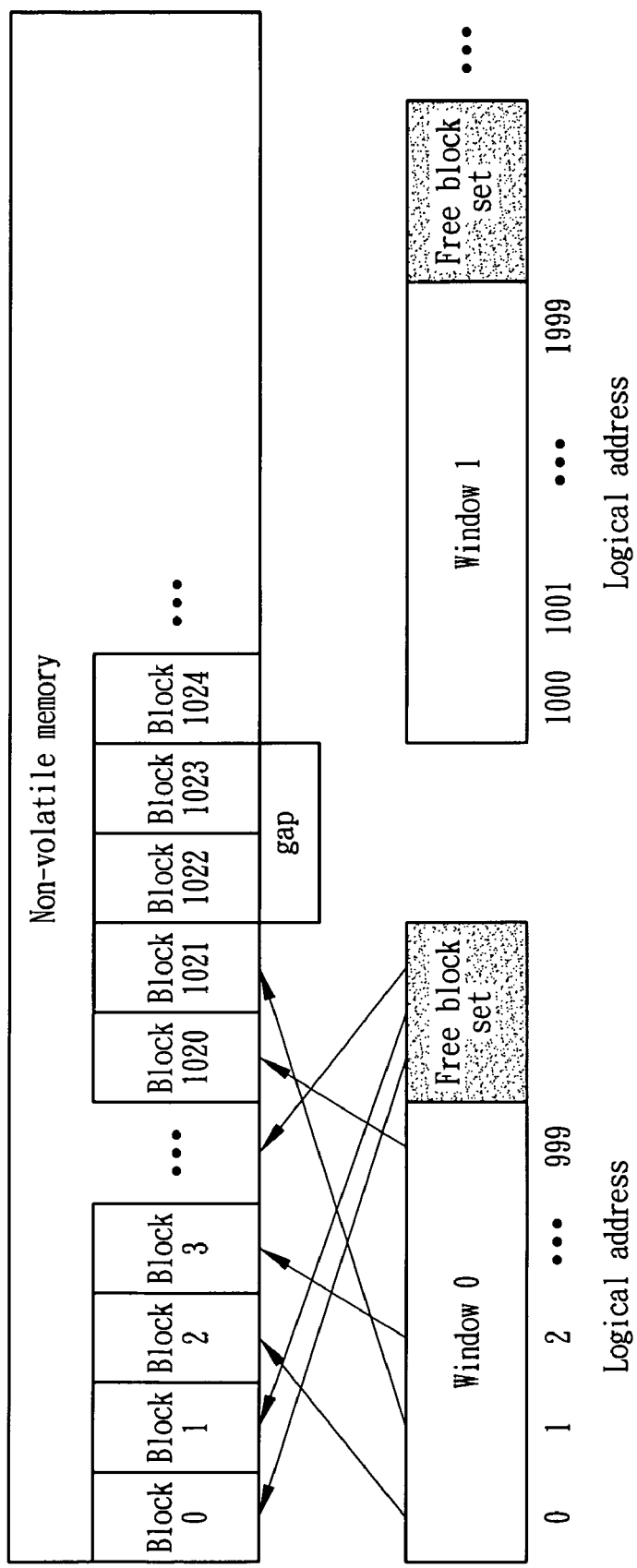
FIG. 6 and FIG. 7 show the method of wear leveling for a non-volatile memory in accordance with a second embodiment of the present invention.

In practice, for the mapping of a wear leveling algorithm, usually the physical blocks do not all map to logical addresses, and some physical blocks do not map to logical addresses, which can be accumulated in a free block set as shown in FIG. 6. The physical blocks to be shifted are allocated to physical blocks in the free block set.

Figure 7:
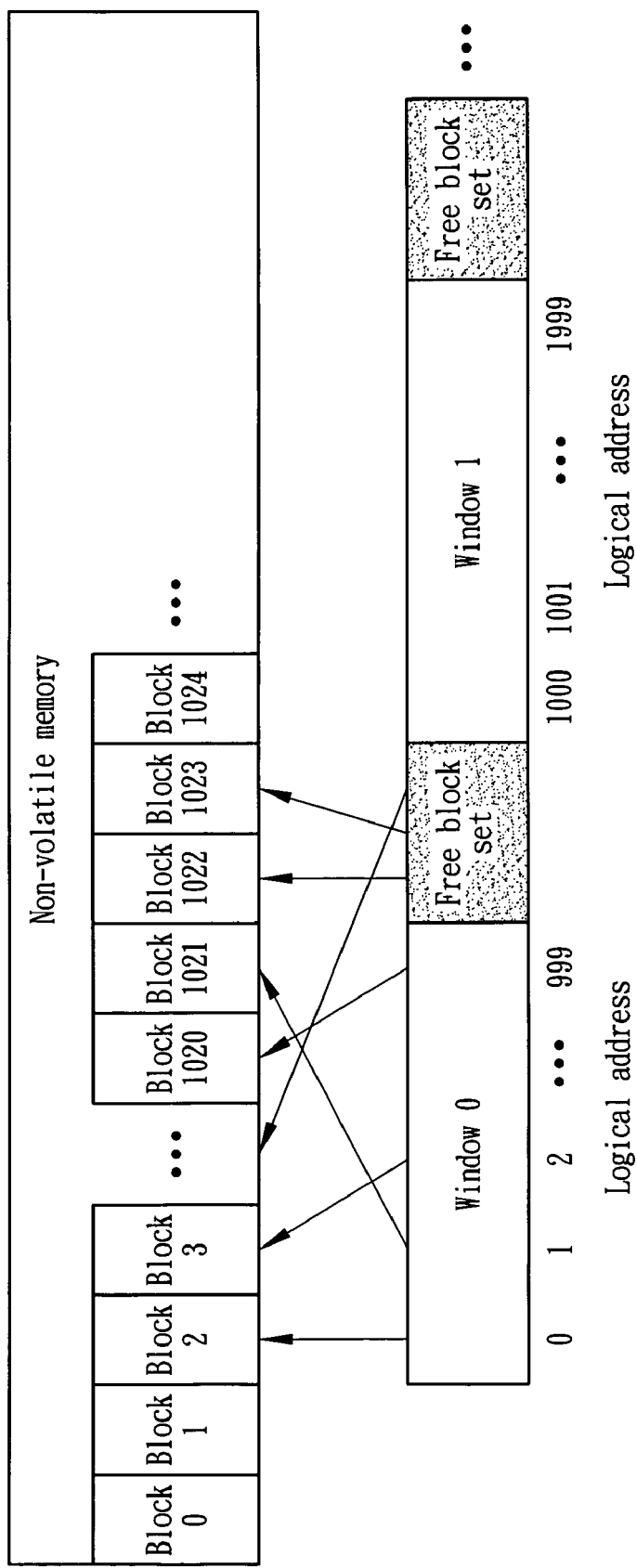

In FIG. 7, window 0 is related to the mapping between 1,000 logical addresses and 1,022 physical blocks. There are 22 physical blocks not mapping to the logical addresses, i.e., the 22 physical blocks are free physical blocks and included in a free block set. When Window 0 performs program/erase 2,400 times, it is very possible to make the physical block 0 and physical block 1 be included in the free block set. When Window 0 begins to shift, the pointer to the free physical blocks 0 and 1 is changed to point to physical blocks 1022 and 1023 in the gap, and no data in the non-volatile memory block needs to be moved. Therefore, no data read/write to the physical blocks is necessary. As a result, the window shift can be performed with minimum operation and cost.

Further referring to FIG. 4, if there are four windows and four gaps, then 1,022×4 logical addresses correspond to 1,024×4 physical blocks for reading/writing. That is, an endurance of the non-volatile memory device having the non-volatile memory of (1,024×4)/(1,022×4)−1=0.2% is generated. As such, the appearance volume of the non-volatile memory is decreased due to the presence of the gaps, but the physical blocks in the gap are used also so as to increase the endurance.

Figure 8:
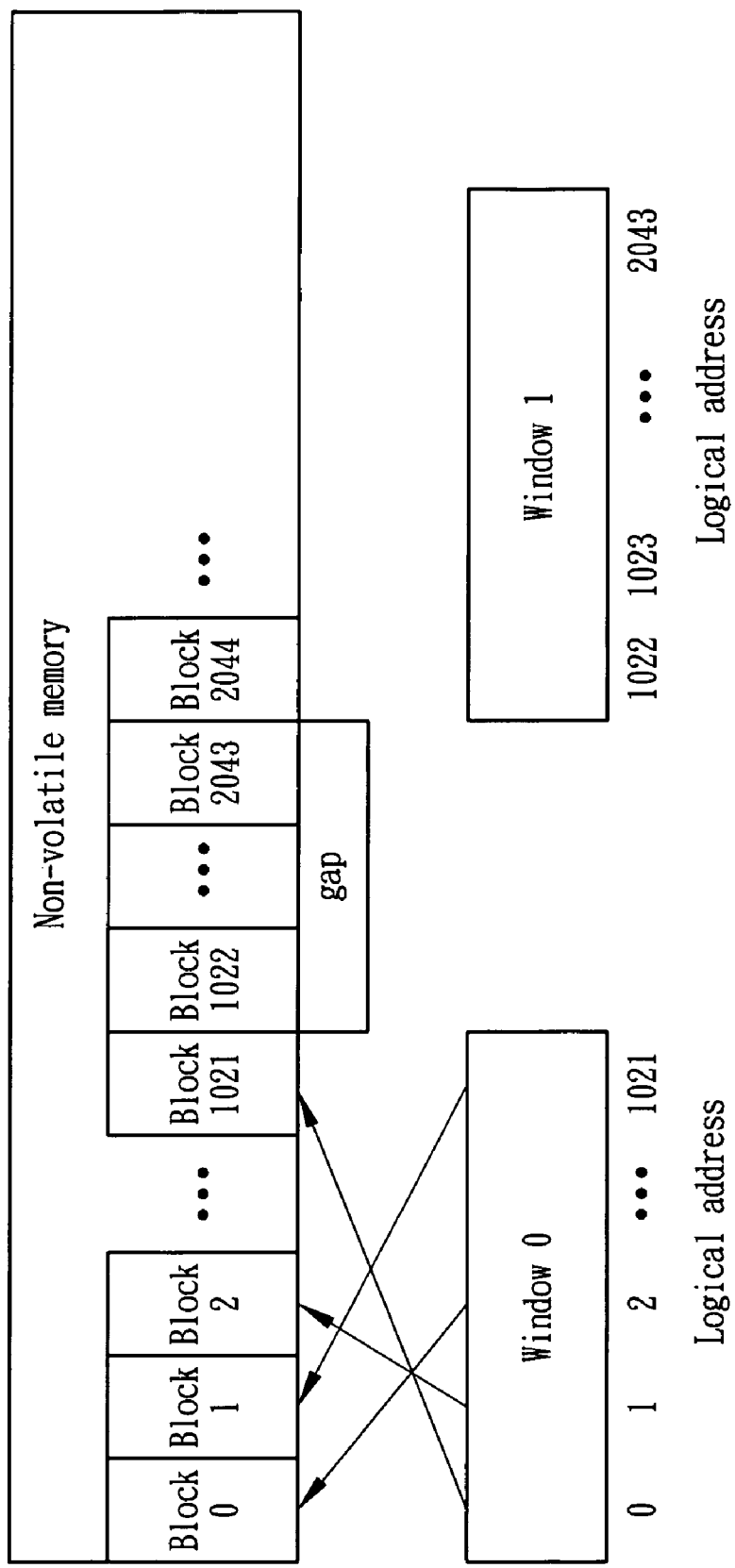
FIG. 8 shows the method of wear leveling for a non-volatile memory device of higher endurance in accordance with an embodiment of the present invention.

Consequently, changes to the gap size can easily increase the endurance of the non-volatile memory device, e.g., an SD card, having the non-volatile memory. As shown in FIG. 8, given that the gap is increased to have 1,022 physical blocks (physical block 1022 to physical block 2043), although it shows 1,022×4 logical addresses, the read/write can be performed on 1,022×8 physical addresses evenly. As such, the endurance is increased twofold.

Moreover, the increase of gap size has further advantages, especially for customization. For example, a flash memory, having a window of 1,000 logical addresses corresponding to 1,024 physical blocks, may not operate normally if 25 physical blocks are damaged. Nevertheless, if there are too many defeated blocks, the window can shift if gaps exist until the window includes more than 1,000 useable physical blocks in the window.

The above-described embodiments of the present invention are intended to be illustrative only. Numerous alternative embodiments may be devised by those skilled in the art without departing from the scope of the following claims.

What is claimed is:

1. A method of wear leveling for a non-volatile memory, the non-volatile memory comprises a plurality of physical blocks, the method comprising the steps of:

dividing the plurality of physical blocks of the non-volatile memory into windows and gaps, wherein the gaps are between the windows, each of the windows comprises physical blocks mapped to logical addresses of a host, and each of the gaps comprises physical blocks not mapped to logical addresses of the host; and shifting one window to an adjacent window through the non-volatile memory in circle to reduce the physical blocks of the gap between the window and the adjacent window, wherein at least one of the logical addresses pointing to the physical block in the window to be shifted is changed to point to the physical block in the gap and the physical block in the window to be shifted is changed to form the gap by not mapping to the logical addresses such that data is not saved in the physical block in the window to be shifted after shifting.

2. The method of claim 1, wherein the physical blocks to be shifted are the initial physical blocks in the window.

3. The method of claim 1, further comprising the step of performing wear leveling in each window before shifting.

4. The method of claim 1, wherein the shifting is performed after the non-volatile memory is erased and/or programmed a predetermined number of times.

5. The method of claim 1, wherein the windows are shifted through the entire non-volatile memory at least once before an erase/program endurance of a non-volatile memory device having the non-volatile memory is expired.

6. The method of claim 1, wherein the gaps are changeable to adjust an endurance of a non-volatile memory device having the non-volatile memory.

7. The method of claim 1, wherein the shifting continues if the quantity of physical blocks in the window capable of being erased and/or programmed is insufficient.

8. A method of wear leveling for a non-volatile memory, the non-volatile memory comprises a plurality of physical blocks, the method comprising the steps of:
dividing the plurality of physical blocks of the non-volatile memory into windows and gaps, wherein the gaps are between the windows, each of the windows comprises physical blocks mapped to logical addresses of a host and free physical blocks not mapped to logical addresses, and each of the gaps comprises physical blocks not mapped to logical addresses of the host;
allocating the physical blocks in the window to be shifted to the free physical blocks; and
shifting one window to an adjacent window through the non-volatile memory to reduce the physical blocks of the gap between the window and the adjacent window, wherein pointers to the free physical blocks in the window are changed to point to the physical blocks in the gap, and the physical block in the window to be shifted is changed to form the gap by not mapping to the logical addresses such that data is not saved in the physical block in the window to be shifted after shifting.

9. The method of claim 8, further comprising the step of performing wear leveling in each window before shifting.

10. The method of claim 8, wherein the shifting is performed after the non-volatile memory is erased and/or programmed a predetermined number of times.

11. The method of claim 8, wherein the windows are shifted through the entire non-volatile memory at least once before an erase/program endurance of a non-volatile memory device having the non-volatile memory is expired.

12. The method of claim 8, wherein sizes of the gaps are changeable to adjust an endurance of a non-volatile memory device having the non-volatile memory.

13. The method of claim 8, wherein the shifting continues if the quantity of physical blocks in the window capable of being erased and/or programmed is insufficient.

14. A wear leveling apparatus for a non-volatile memory, comprising:
a host;
a non-volatile memory; and
an address converter configured to convert logical addresses from the host into physical addresses directed to a plurality of physical blocks of the non-volatile memory, the address converter comprising a memory that stores mapping information between the logical addresses and the physical blocks,
wherein the non-volatile memory is divided into a plurality of windows and gaps between the windows, and one window is shifted to an adjacent window through the non-volatile memory to reduce the physical blocks of the gap between the windows and the adjacent window after being erased or programmed a predetermined number of times,
wherein the physical block in the window to be shifted is changed to form the gap by not mapping to the logical addresses such that data is not saved in the physical block in the window to be shifted after shifting.

15. The wear leveling apparatus of claim 14, wherein the non-volatile memory further comprises gaps between the windows, the windows comprise the physical blocks mapped to logical addresses, the gaps comprise the physical blocks not mapped to logical addresses, and the logical addresses pointing to the physical blocks in the window to be shifted are changed to point to the physical blocks in the gap when shifting.

16. The wear leveling apparatus of claim 14, wherein the non-volatile memory further comprises gaps between the windows, the windows comprise physical blocks mapped to logical addresses and free physical blocks not mapped to logical addresses, and the gaps comprise physical blocks not mapped to logical addresses, the physical blocks in the window to be shifted are allocated to be the free physical blocks, and pointers to the free physical blocks are changed to point to the physical blocks in the gap when shifting.

* * * * *